United States Patent
Bucher et al.

(10) Patent No.: US 9,915,673 B2
(45) Date of Patent: Mar. 13, 2018

(54) TUBE RACK TRANSFER DEVICE AND DIAGNOSTIC INSTRUMENT

(71) Applicant: Roche Diagnostics Operations, Inc., Indianapolis, IN (US)

(72) Inventors: Marco Bucher, Hohenrain (CH); Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/561,283

(22) Filed: Dec. 5, 2014

(65) Prior Publication Data

US 2015/0160249 A1 Jun. 11, 2015

(30) Foreign Application Priority Data

Dec. 10, 2013 (EP) .................................. 13196392

(51) Int. Cl.
*G01N 35/02* (2006.01)
*B65G 47/82* (2006.01)
(Continued)

(52) U.S. Cl.
CPC ........... *G01N 35/026* (2013.01); *B65G 47/82* (2013.01); *G01N 35/04* (2013.01); *B65G 25/08* (2013.01);
(Continued)

(58) Field of Classification Search
CPC ............ B65G 2201/0235; B65G 25/08; B65G 2812/12; B65G 47/82; G01N 2035/0415; G01N 35/026; Y10T 436/113332
See application file for complete search history.

(56) References Cited

U.S. PATENT DOCUMENTS 4,099,921 A * 7/1978 Allington .............. B01L 7/5255
422/67
6,331,437 B1 * 12/2001 Cohen .................... G01N 35/04
422/509
(Continued)

FOREIGN PATENT DOCUMENTS

| CN | 202735359 U | 2/2013 |
|---|---|---|
| EP | 0979999 A2 | 2/2000 |
| EP | 2620776 A1 | 7/2013 |

*Primary Examiner* — Sean E Conley
*Assistant Examiner* — Benjamin R Whatley
(74) *Attorney, Agent, or Firm* — Roche Diagnostics Operations, Inc.

(57) ABSTRACT

A tube rack transfer device for transferring racks is presented. A first rail extends in a first horizontal direction and a second rail extends in a second horizontal direction orthogonal to the first direction. The second rail moves along the first rail and comprising a transfer head movable along the second rail. The transfer head comprises a control pin to be coupled with one of: an input pusher, translatable in the second direction, for transferring a rack from a carrier to a sampling area of an analyzer; an output pusher for transferring a rack from the sampling area to a carrier; a rack for transferring the rack between different carriers and/or between different positions of the same carrier. An in-vitro diagnostic instrument comprises an analyzer for carrying out tests on biological samples, a sample unit for inputting/outputting racks, a sampling area for withdrawing samples from tubes, and a transfer device.

13 Claims, 14 Drawing Sheets

(51) Int. Cl.
  *B65G 25/08*  (2006.01)
  *G01N 35/04*  (2006.01)
(52) U.S. Cl.
  CPC ........... *B65G 2201/0235* (2013.01); *G01N 2035/0415* (2013.01); *G01N 2035/0475* (2013.01)

(56) References Cited

U.S. PATENT DOCUMENTS

| | | | |
|---|---|---|---|
| 6,521,183 B1* | 2/2003 | Burri | G01N 35/026 422/65 |
| 6,586,255 B1* | 7/2003 | Hubert | G01N 35/0099 422/504 |
| 7,115,090 B2 | 10/2006 | Lagarde | |
| 2005/0196320 A1* | 9/2005 | Veiner | G01N 35/04 422/63 |
| 2006/0216199 A1* | 9/2006 | Koike | G01N 35/026 422/65 |
| 2009/0162247 A1* | 6/2009 | Tokieda | G01N 35/026 422/65 |
| 2010/0028203 A1* | 2/2010 | Frey | G01N 35/0099 422/65 |
| 2010/0166606 A1 | 7/2010 | Koike et al. | |
| 2011/0250091 A1* | 10/2011 | Kaiga | G01N 35/04 422/63 |
| 2015/0260746 A1* | 9/2015 | Pedrazzini | G01N 35/0099 414/225.01 |

* cited by examiner

TUBE RACK TRANSFER DEVICE AND DIAGNOSTIC INSTRUMENT

CROSS-REFERENCE TO RELATED APPLICATIONS

This application is a continuation of EP 13196392.8, filed Dec. 10, 2013, which is hereby incorporated by reference.

BACKGROUND

The present disclosure generally relates to the field of biochemical research, biochemical routine analytics, clinical diagnostics and clinical research and, in particular, to a tube rack transfer device for transferring tube racks and an in-vitro diagnostic instrument comprising at least one such tube rack transfer device.

In recent years, automated analytical instruments ("analyzers") offering a variety of analytical methods have become commercially available. Modern analyzers usually can process samples in standard sample vessels such as sample tubes which allow for an easy and cost-effective sample analysis. In order to process many samples in a batch-wise or continuous manner, it is known to arrange plural sample tubes in dedicated tube holders usually referred to as "racks" which are transported in the automated instrument for sample analysis.

Therefore, there is a need to provide a device for transferring tube racks and an in-vitro diagnostic instrument which is simple and robust in construction, can be easily controlled as well as manufactured and maintained in cost-efficient manner.

SUMMARY

According to the present disclosure, a tube rack transfer device for transferring tube racks is disclosed. The tube rack transfer device comprises a first rail extending in a first horizontal direction and a second rail extending in a second horizontal direction orthogonal to the first horizontal direction. The second rail is movable along the first rail and comprises at least one transfer head movable along the second rail. The transfer head comprises at least one control pin adapted to be coupled with at least one of: an input pusher translatable in the second direction for transferring a tube rack from a rack carrier to a sampling area of a diagnostic instrument, an output pusher for transferring a tube rack from a sampling area of a diagnostic instrument to a rack carrier, and a tube rack for transferring the tube rack between different rack carriers and/or between different positions of the same rack carrier.

In accordance with one embodiment of the present disclosure, an in-vitro diagnostic instrument is disclosed. The in-vitro diagnostic instrument comprises at least one analytical area for carrying out in-vitro diagnostic tests on biological samples, at least one sample unit for inputting/outputting tube racks, a sampling area for withdrawing samples from sample tubes, and at least one tube rack transfer device for transferring tube racks.

Accordingly, it is a feature of the embodiments of the present disclosure to provide a device for transferring tube racks and an in-vitro diagnostic instrument which is simple and robust in construction, can be easily controlled as well as manufactured and maintained in cost-efficient manner. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
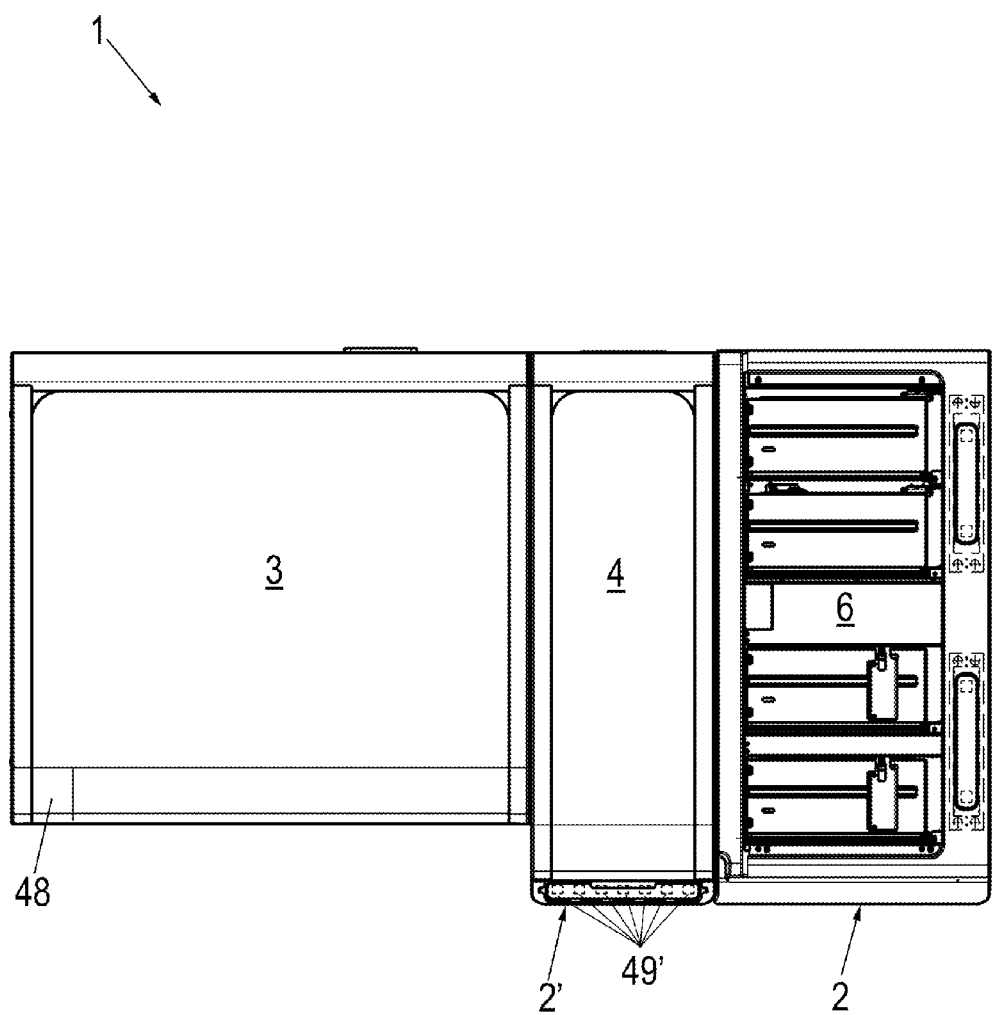
FIG. 1 illustrates a top view of a diagnostic instrument according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A "sample tube", herein interchangeably referred to as "tube", can either be a sample collection test tube, also called "primary tube", used to receive a sample from a patient and to transport the sample contained therein to an analytical laboratory for diagnostics purposes, or a "secondary tube", which may be used to receive an aliquot of sample from a primary tube. A primary sample tube can typically be made of glass or plastic, can have a closed end and an open end, typically closed by a closure. A secondary tube can typically be made of plastics and may have a lower degree of variation of size and type with respect to primary tubes. In particular, secondary tubes may be smaller than primary tubes and may be designed to be closed with one type or similar types of closure, for example, the screw type. The test tube can, for example, be a tubular test tube which may, for example, have a cylindrical shaft closed on the bottom side by a rounded, e.g. hemispherical, bottom.

A "tube rack", herein interchangeably referred to as "rack," can relate to a tube holder provided with a plurality of tube seats for holding test tubes. The tube rack can, for example, be configured to hold test tubes in an upright manner, for example, aligned in a row.

A new device for transferring tube racks is presented. The tube rack transfer device can comprise a first rail extending a first direction and a second rail extending in a second direction orthogonal to the first direction with the second rail movable along the first rail and the transfer head movable along the second rail. At least one transfer head can be movably fixed to the second rail in a manner to be movable along the second rails. Specifically, the transfer head can comprise at least one control pin to be coupled with at least one of: an input pusher, translatable in the second direction, for transferring a tube rack from a rack carrier to a sampling area of an in-vitro diagnostic instrument; an output pusher for transferring a tube rack from a sampling area of an in-vitro diagnostic instrument to a rack carrier; and a tube rack for transferring the tube rack between different rack carriers and/or between different positions of the same rack carrier.

In one embodiment, the device for transferring tube racks can comprise a transfer lane extending along the first horizontal direction and arranged between at least two rack carriers in such a manner that a tube rack can be transferred between different rack carriers and/or between a rack carrier and the sampling area via the transfer lane.

In one embodiment of the device for transferring tube racks, the second rail can comprise a transfer lane pin linearly translatable together with the second rail in the first horizontal direction for moving a tube rack along the transfer lane.

In one embodiment, the device for transferring tube racks can comprise a rack transport shuttle for transporting a tube rack arranged in a manner to receive/provide a tube rack from/to the transport lane.

In one embodiment of the device for transferring tube racks, the transfer head can comprise an input pusher control pin to be coupled with at least one input pusher and an output pusher control pin to be coupled with at least one output pusher.

In one embodiment of the device for transferring tube racks, the transfer head can comprise an input pusher fixation control pin to be coupled with at least one input pusher for releasing a fixation mechanism capable of preventing the input pusher to be translated in the second direction.

In one embodiment of the device for transferring tube racks, the output pusher can be configured to be tiltable in the second direction for pushing tube racks.

A new in-vitro diagnostic instrument for analyzing samples is presented. The instrument can be configured to analyze samples with respect to one or more analytical methods. The diagnostic instrument can comprise at least one analytical area for carrying out in-vitro diagnostic tests on biological samples. The instrument can further comprise at least one sample unit for inputting/outputting tube racks and a sampling area for withdrawing samples from sample tubes. The instrument can yet further comprise at least one transfer device for transferring tube racks according to one or more of the above-described embodiments.

In one embodiment of the diagnostic instrument, the sample unit can comprise an input carrier section, provided with one or more input carrier supports, each of which can support a rack carrier for holding tube racks to be supplied to the sampling area with each of the input carrier supports coupled to an input pusher. The sample unit can further comprise an output carrier section, provided with one or more output carrier supports, each of which can support a rack carrier for holding tube racks to be received from the sampling area or the input carrier section with each of the output carrier supports coupled to an output pusher.

In one embodiment of the diagnostic instrument, the input carrier section and the output carrier section can be coupled to a transfer lane to transfer tube racks from the input carrier section to the sampling unit or output carrier section and to transfer tube racks from the sampling unit to the output carrier section.

In one embodiment of the diagnostic instrument, each rack carrier can comprise a tube rack guide for guiding tube racks, for example, aligned in a row.

In one embodiment of the diagnostic instrument, the sampling area can comprise one or more slots for supporting tube racks.

In one embodiment, the diagnostic instrument can comprise a first tube rack transfer device arranged underneath the sample unit and a second tube rack transfer device arranged underneath the sampling area.

An exemplary in-vitro diagnostic instrument, generally referred to under reference numeral 1, can be configured to analyze samples with respect to one or more analytical methods involving the use of sample tubes 5. Description is also given for a tube rack transfer device, generally referred to under reference numeral 2, 2', for the automated transfer of tube racks 7 in the diagnostic instrument 1.

With particular reference to FIGS. 1 to 4, the diagnostic instrument 1 can comprise at least one analytical area 3 for carrying out in-vitro diagnostic tests on biological samples, a sampling area 4 for withdrawing samples from sample tubes 5, and at least one sample unit 6 for inputting/outputting tube racks 7. Accordingly, tube racks 7 provided with sample tubes 5 containing biological samples can be supplied to the instrument 1 using the sample unit 6 with the samples being withdrawn from the sample tubes 5 in the sampling area 4 so as to be analyzed in the analytical area 3.

As schematically illustrated in FIG. 1, the instrument 1 can further comprise two tube rack transfer devices 2, 2', with a first tube rack transfer device 2 arranged underneath the sample unit 6 for transferring tube racks 7 in the sample unit 6 and a second tube rack transfer device 2' arranged underneath the sampling area 4 for transferring tube racks 7 in the sampling area 4.

Figure 2:
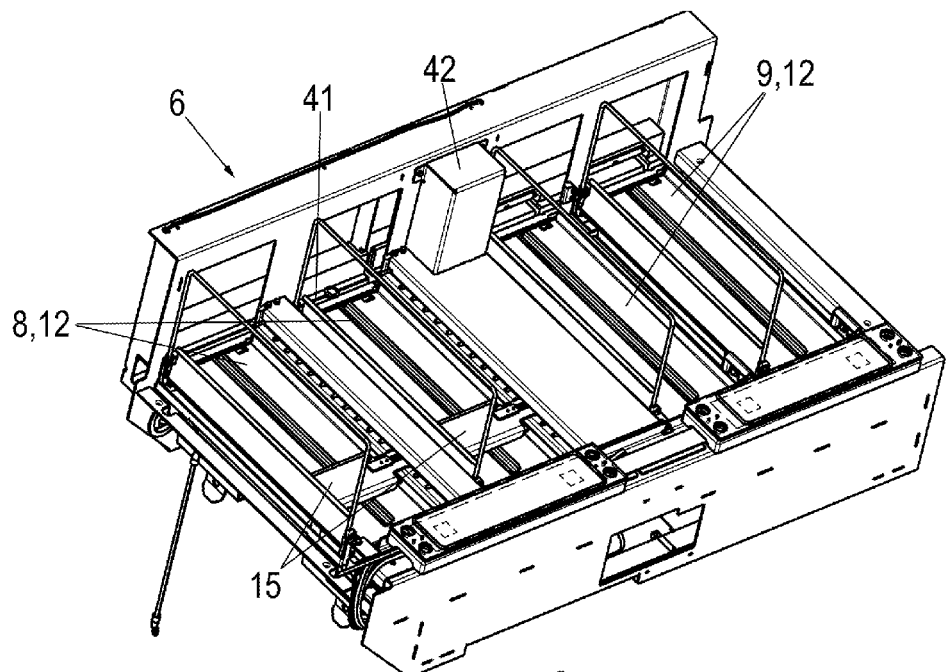
FIG. 2 illustrates a perspective view of the sample unit of the instrument of FIG. 1 according to an embodiment of the present disclosure.
Figure 3:
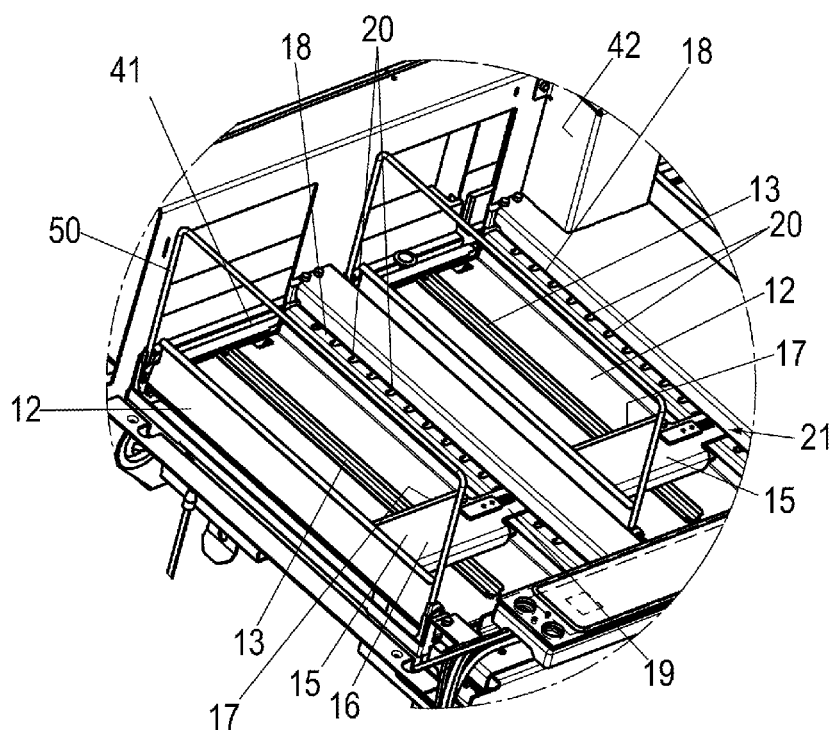
FIG. 3 illustrates an enlarged detail of FIG. 2 according to an embodiment of the present disclosure.
Figure 4:
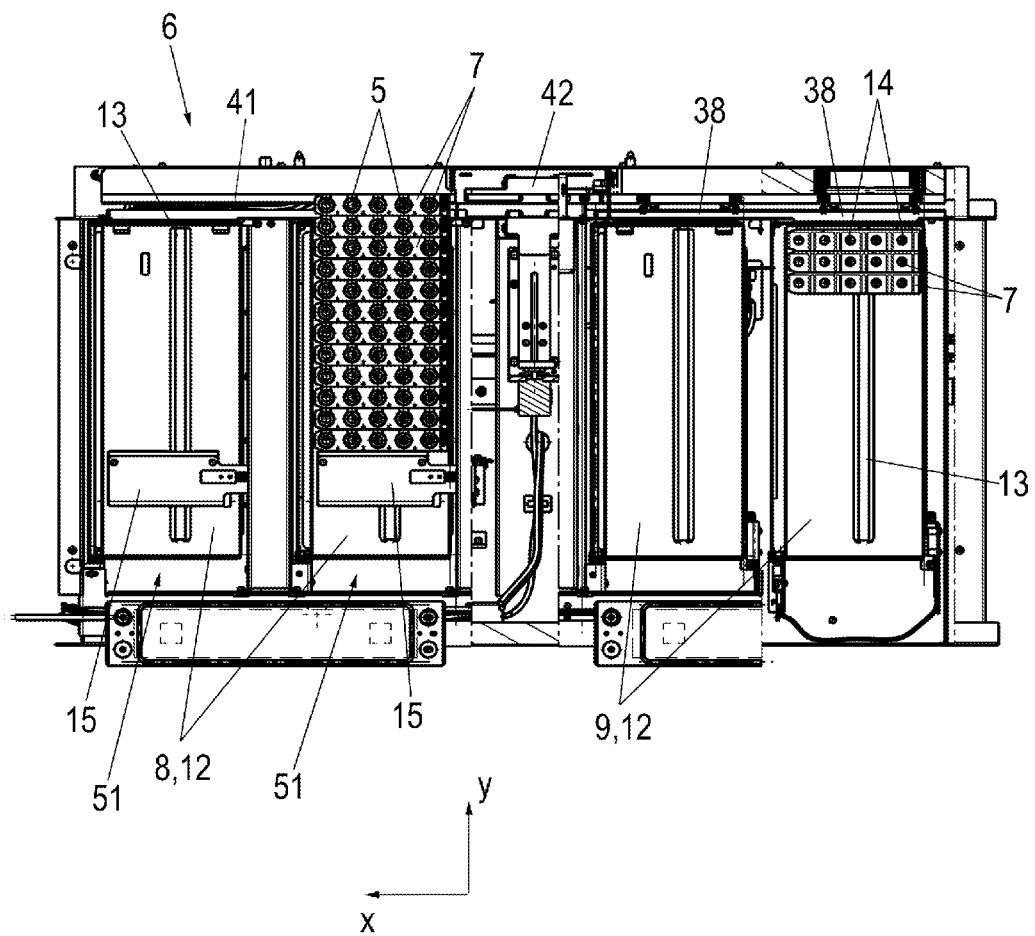
FIG. 4 illustrates a top view of the sample unit of the instrument of FIG. 1 according to an embodiment of the present disclosure.

With particular reference to FIGS. 2, 3 and 4, the sample unit 6 can comprise an input carrier section 8 for supplying tube racks 7 and an output carrier section 9 for removing tube racks 7 with respect to the instrument 1. The input carrier section 8 and the output carrier section 9 can be arranged side by side along a first horizontal direction (x). A transfer lane 41, for transporting tube racks 7, can extend along the first horizontal direction (x) from the input carrier section 8 to the output carrier section 9.

Specifically, the input carrier section 8 can comprise a plurality of input carrier supports 10 (see FIG. 16), each of which can receive one rack carrier 12. Analogously, the output carrier section 9 can comprise a plurality of output carrier supports 11 (see FIG. 15 or 16), each of which can receive one rack carrier 12 in a fixed position. In the embodiment illustrated, both the input carrier section 8 and the output carrier section 9 can have a number of two carrier supports 10, 11. It, however, is to be understood that any other number of carrier supports 10, 11 can be envisaged according to the specific demands of the user, such as, but not limited to, one carrier support 10, 11 or four carrier supports 10, 11 provided in one carrier section 8, 9. The input carrier supports 10 and the output carrier supports 11 can be arranged side by side along the first horizontal direction (x).

In one embodiment, an elongate tube rack 7 can have a plurality of tube seats 14, each of which can hold one sample tube 5 which can be serially arranged with respect to each other along the extension of the tube rack 7. The tube rack 7 can, e.g., be provided with five tube seats 14, however, those of skill in the art can appreciate that any other number of tube seats 14 and arrangement thereof can be envisaged according to the specific demands of the user.

Typically, the sample tubes 5 can be made of glass or plastic and can have a tubular body for receiving liquid closed on the bottom side by a rounded, e.g. hemispherical, bottom. The sample tubes 5 can be inserted into the tube seats 14 in an upright position.

In one embodiment, an elongate rack carrier 12, commonly referred to as "tray", can be configured to receive a plurality of tube racks 7. A rack carrier 12 can receive plural tube racks 7 arranged one after the other along the extension of the rack carrier 12, with the tube seats 14 of a tube rack 7 arranged perpendicularly to the extension of the rack carrier 12. Specifically, the tube racks 7 can be put on the rack carrier 12 in a manner to be guidable (guided) along a rack guide 13 extending along the extension of the rack carrier 12. In one embodiment, the tube racks 7 can be specifically brought in guiding engagement with the rack guide 13. In one embodiment, the rack guide 13 can be configured as a guide rail for slidably guiding the tube racks 7. Accordingly, if a rack carrier 12 is positioned on a carrier support 10, 11, the rack guide 13 can extend along a second direction (y), orthogonally aligned with respect to the first horizontal direction (x), with the tube seats 14 of each tube rack 7 extending along the first horizontal direction (x).

With continued reference to FIGS. 2, 3 and 4, each input carrier support 10 can comprise an individual input pusher 15 for pushing tube racks 7 from a rack carrier 12 positioned on the input carrier support 10 towards and onto the transfer lane 41. For this purpose, the input pusher 15 can be translatably coupled to an elongate pusher guide 18 extending along the second horizontal direction (y), such as but not limited to, a guide rail. Accordingly, the input pusher 15 can be translated along the second direction (y) guided by the pusher guide 18. The input pusher 15 of an input carrier support 10 can be provided with an input pusher contact face 17 positioned towards tube racks 7 on a rack carrier 12 on the input carrier support 10 for pushing the tube racks 7 onto the transfer lane 41. In one embodiment, each input pusher 15 can have an elongate pusher plate 16 extending along the first horizontal direction (x) provided with a chamfered end portion to be used as input pusher contact face 17 for pushing tube racks 7, with the pusher plate 16 coupled to the pusher guide 18 via a strut 19. Each input pusher 15 can be moved to a parking area 51 so as to provide free access to the corresponding input carrier support 10 in order to put a rack carrier 12 on the input carrier support 10 or to remove it therefrom.

Figure 8:
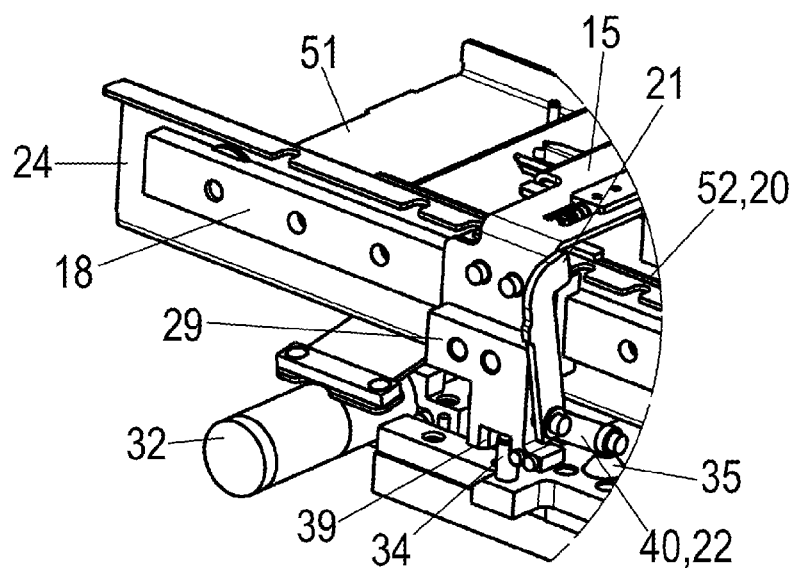
FIG. 8 illustrates an enlarged detail of FIG. 7 according to an embodiment of the present disclosure.
Figure 10:
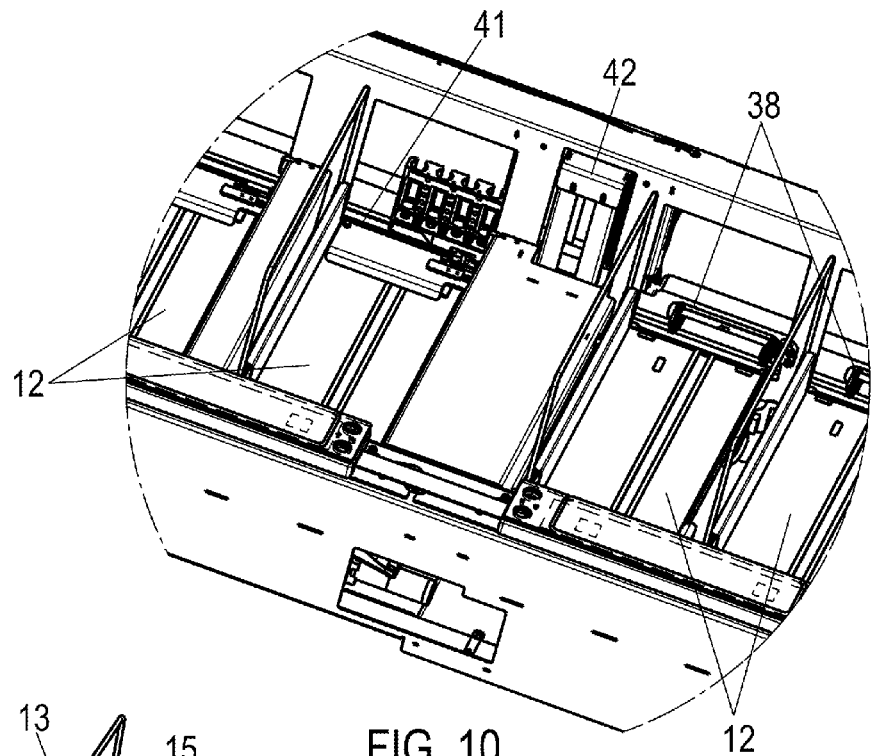
FIG. 10 illustrates an enlarged detail of FIG. 9 according to an embodiment of the present disclosure.
Figure 9:
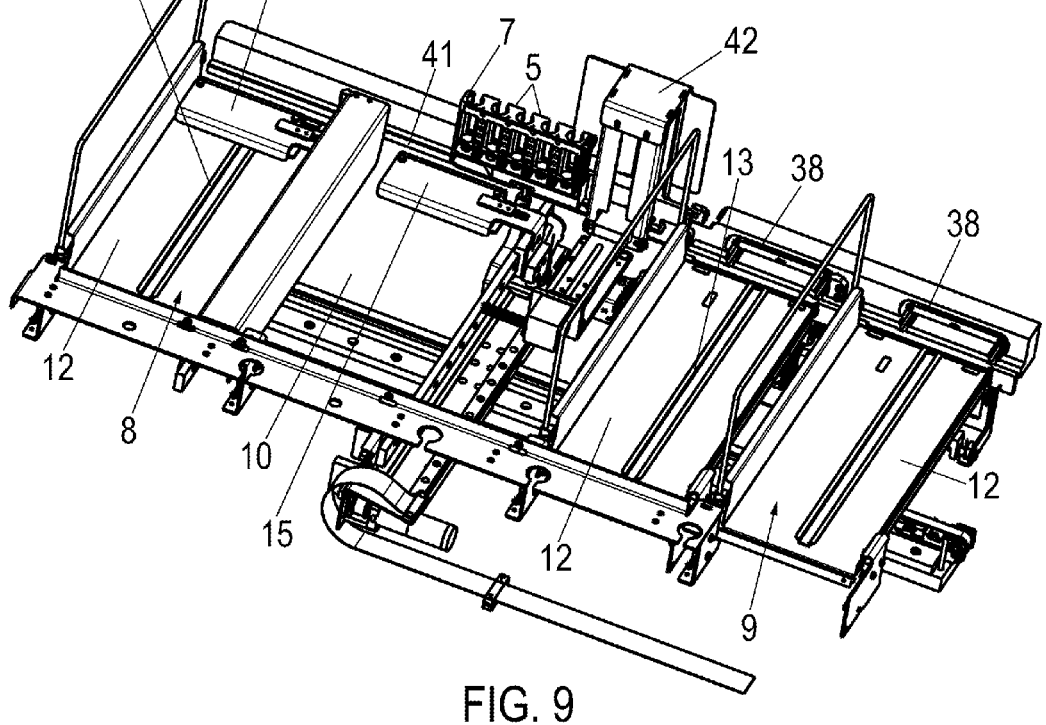
FIG. 9 illustrates a perspective view of the sample unit of the instrument of FIG. 1 illustrating the rack transport shuttle according to an embodiment of the present disclosure.
Figure 11:
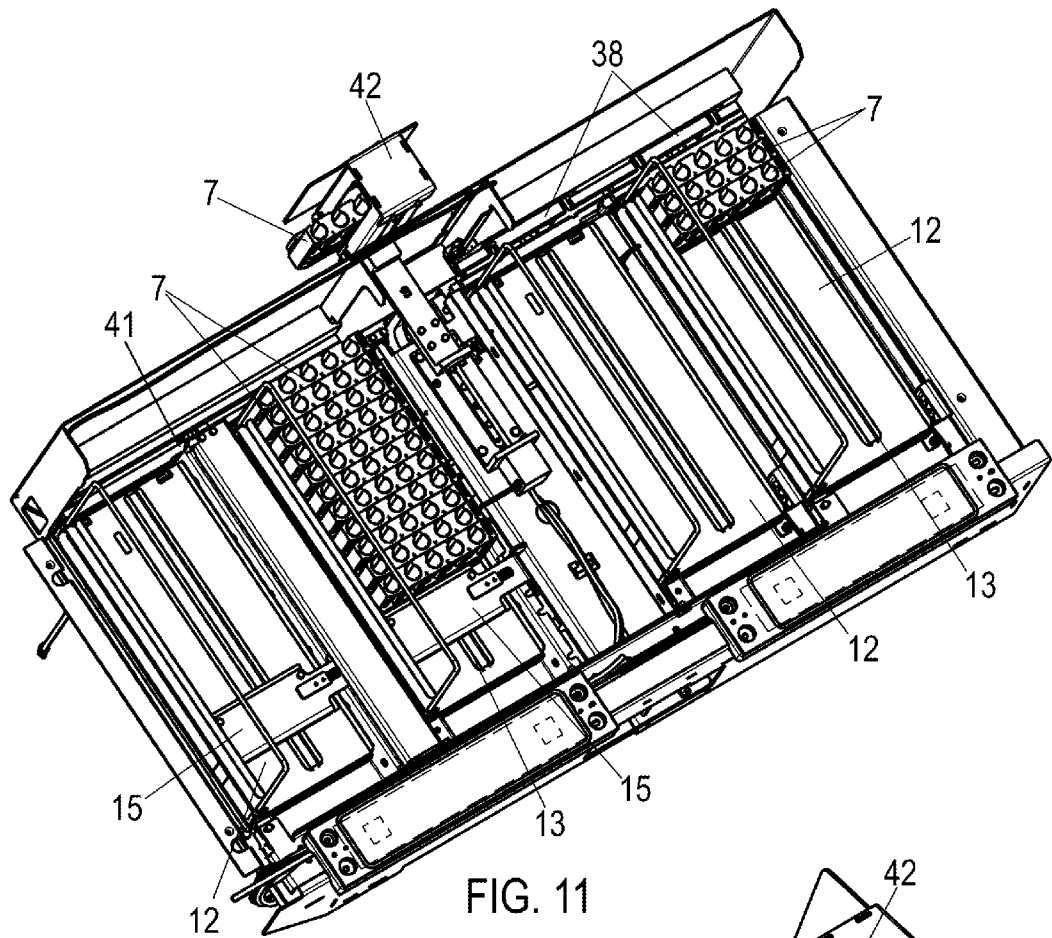
FIG. 11 illustrates another perspective view of the sample unit of the instrument of FIG. 1 illustrating the rack transport shuttle according to an embodiment of the present disclosure.
Figure 12:
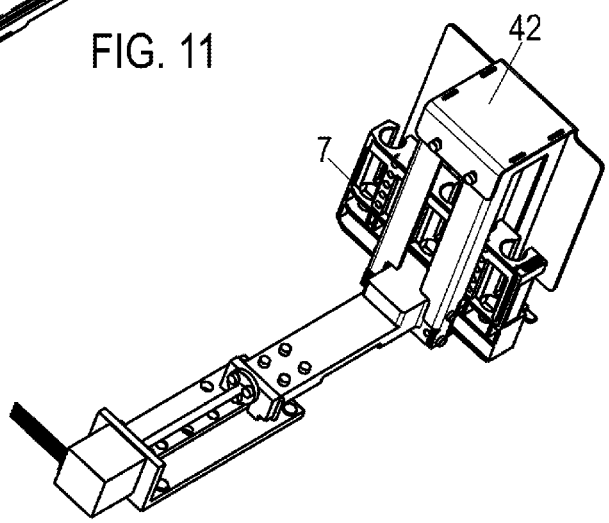
FIG. 12 illustrates the rack transport shuttle of the sample unit of the instrument of FIG. 1 according to an embodiment of the present disclosure.

With reference to FIG. 8, the input pushers 15 can be fixed in various stop positions as given by first engagement elements 20 relative to the second horizontal direction (y) by an input pusher fixation mechanism 52. The first engagement elements 20 can be engaged with second engagement elements 21 of the input pusher 15. In one embodiment, the pusher guide 18 can be provided with plural fixation recesses 20 as first engagement elements for inserting a fixation crotchet 21 as second engagement element 21 of the input pusher 15. The input pusher 15 can further comprise a release mechanism 22 which can be operated for releasing the fixation of the input pusher 15. In one embodiment, the release mechanism 22 can be configured to pull the fixation crotchet 21 out of a fixation recess 20, in particular, against the resilient force of a resilient member.

Figure 5:
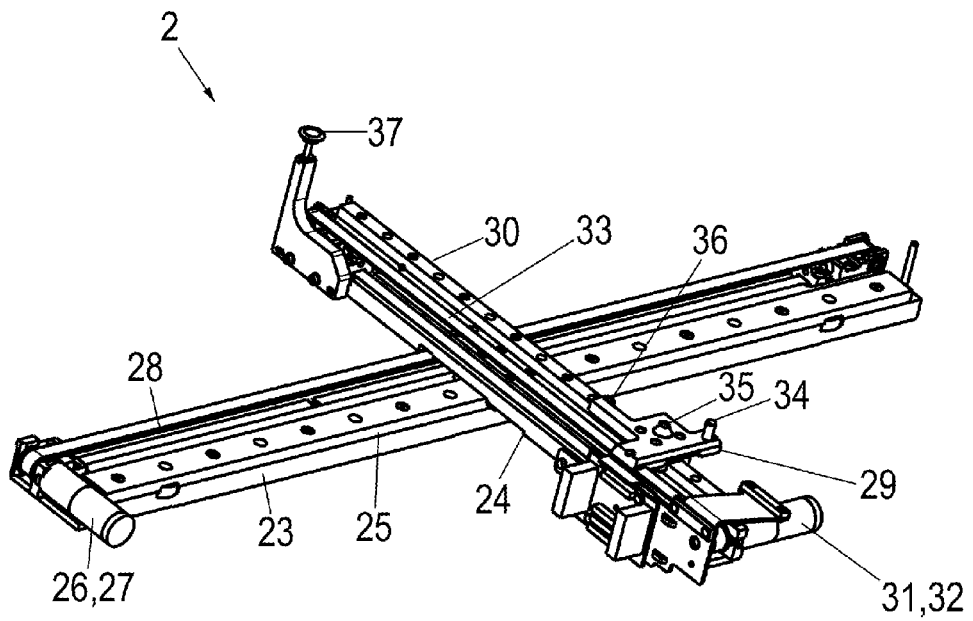
FIG. 5 illustrates a perspective view of the tube rack transfer device of the sample unit of the instrument of FIG. 1 according to an embodiment of the present disclosure.
Figure 6:
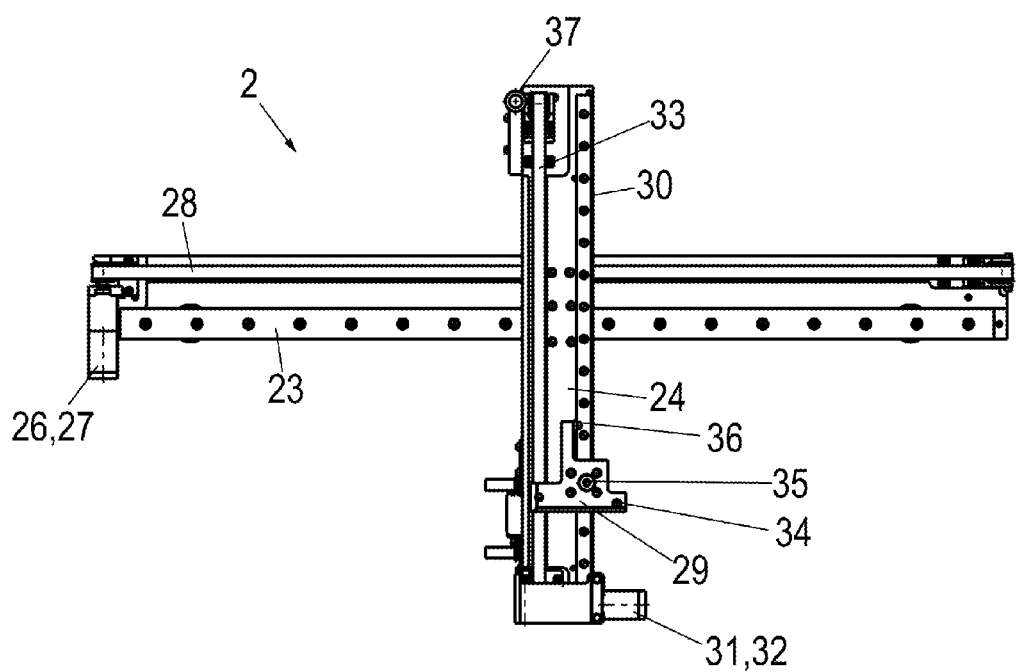
FIG. 6 illustrates a top view of the tube rack transfer device of FIG. 5 according to an embodiment of the present disclosure.

With reference to FIGS. 5 and 6, the input pusher 15 can be translated by the first tube rack transfer device 2 comprising a horizontal two-rail moving mechanism. A first rail 23 can extend in the first horizontal direction (x) and a second rail 24 can extend in the second horizontal direction (y), with the second rail 24 translatably fixed to the first rail 23 so as to be translatable along the first rail 23. The first rail 23 can be provided with a rail guide 25 extending along the first rail 23 for guiding the second rail 24, with the second rail 24 engaged with the rail guide 25. Accordingly, the second rail 24 can be translated along the first rail 23. A first moving mechanism 26 such as, for example, a first electric motor 27 rotatably coupled to a first belt drive 28, can be operated to automatically translate the second rail 24 along the first rail 23.

Furthermore, the second rail 24 can be provided with a transfer head 29, with the transfer head 29 translatably fixed to the second rail 24 so as to be translatable along the second rail 24. The second rail 24 can be provided with a transfer head guide 30 extending along the second rail 24 for guiding of the transfer head 29, with the transfer head 29 engaged with the transfer head guide 30. Accordingly, the transfer head 29 can be translated along the second rail 24. A second moving mechanism 26 such as, for example, a second electric motor 28 rotatably coupled to a second belt drive 33, can be operated to translate the transfer head 29 along the second rail 24. Accordingly, the transfer head 29 can be moved over a horizontal plane having components of travel in the first horizontal direction (x) and/or the second horizontal direction (y).

In one embodiment, the transfer head 29 can be provided with various control pins for controlling movements of the tube racks 7. In one embodiment, the transfer head 29 can be provided with an input pusher control pin 34 coupled with an input pusher 15 for moving of the input pusher 15 and an input pusher fixation control pin 35 coupled with an input pusher 15 for releasing of the input pusher fixation mechanism 52 so that the input pusher 15 can be translated in the second horizontal direction (y). The transfer head 29 can further comprise an output pusher control pin 36 coupled with an output pusher 38 as described further below. Furthermore, the second rail 24 can be provided with a transfer lane pin 37 which can be linearly translatable together with the second rail 24 in the first horizontal direction (x). In the embodiment shown, the input pusher control pin 34, the input pusher fixation control pin 35 and the transfer lane pin 37 can project orthogonally (upwards) relative to the horizontal plane spanned by the first and second horizontal directions (x, y). Contrary thereto, the output pusher control pin 36 can project in the first horizontal direction (x).

Figure 7:
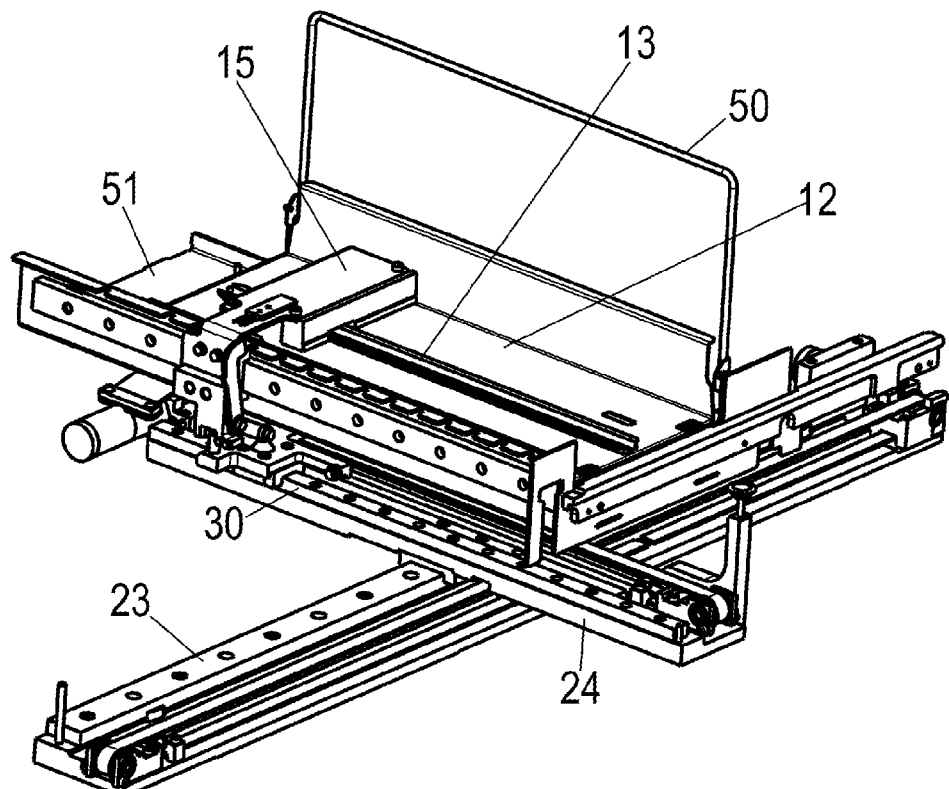
FIG. 7 illustrates a perspective view of the tube rack transfer device of FIG. 5 coupled to a rack carrier according to an embodiment of the present disclosure.

With particular reference to FIGS. 7 and 8, an input pusher 15 can be translated by moving the input pusher control pin 34. Each input pusher 15 can be provided with an input pusher control pin recess 39 opening in the first horizontal direction (x) so that the input pusher control pin 34 can readily be inserted by moving the transfer head 29 in the first horizontal direction (x). Accordingly, the input pusher 15 can be moved in the second horizontal direction (y) by moving the transfer head 29 in the second horizontal direction (y).

With reference to FIG. 8, the input pusher fixation control pin 35 can be used to release the input pusher fixation mechanism 52 so as to enable a translational movement of the input pusher 15. By inserting the input pusher control pin 34 in the input pusher control pin recess 39, the input pusher fixation control pin 35 can simultaneously be brought in contact with a turning lever 40 coupled to the release mechanism 22 in a manner to release the fixation of the input pusher 15. In one embodiment, by turning the turning lever 40 by pushing the input pusher fixation control pin 35 against the turning lever 40, the fixation of the input pusher 15 can be released by pulling the fixation crotchet 21 out of a fixation recess 20, in particular, against the resilient force of a resilient element. In the latter case, if the contact between the input pusher fixation control pin 35 and the turning lever 40 is released, the turning lever 40 can be turned back by the resilient force of the resilient element so as to insert the fixation crotchet 21 in another fixation recess 20 for fixing the input pusher 15.

Accordingly, a tube rack 7 can be pushed from a rack carrier 12 on the transfer lane 41 by moving the input pusher 15 towards the transfer lane 41. If positioned on the transfer lane 41, a tube rack 7 can be translated along the transfer lane 41 by moving the transfer lane pin 37 which can be engaged with a tube rack recess 58 (see FIGS. 21 and 22). In one embodiment, the transfer lane pin 37 can automatically be brought in engagement with the tube rack recess 58 of a tube rack 7 when pushed on the transfer lane 41 by moving the transfer head 29. As a result, a tube rack 7 on the transfer lane 41 can be translated in the first direction (x) by moving the transfer lane pin 37 by moving the second rail 24. Accordingly, a tube rack 7 can be transported from a rack carrier 12 of the input carrier section 8 along the first direction (x).

With reference to FIGS. 9 to 12, a rack transport shuttle 42 for transporting tube racks 7 can be coupled to the transfer lane 41 in a position between the input carrier section 8 and the output carrier section 9. The rack transport shuttle 42 can be configured to receive a tube rack 7 from the transfer lane 41 or to supply a tube rack 7 to the transfer lane 41. Furthermore, the rack transport shuttle 42 can be moved between the transport lane 41 and the sampling area 4 in order to transport tube racks 7 to and away from the sampling area 4. Accordingly, using the rack transport shuttle 42 coupled to the transfer lane 41, tube racks 7 can be transported from the input carrier section 8 to the sampling area 4 and from the sampling area 4 to the output carrier section 9.

Figure 13:
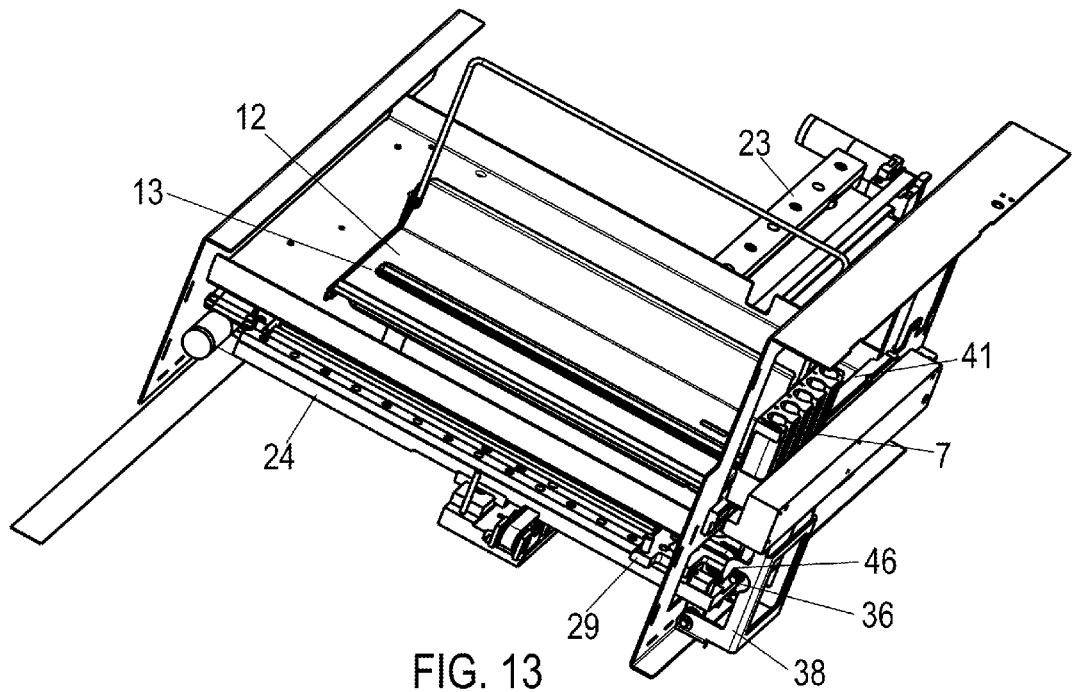
FIG. 13 illustrates a perspective view of the output carrier section of the sample unit of the instrument of FIG. 1 according to an embodiment of the present disclosure.
Figure 14:
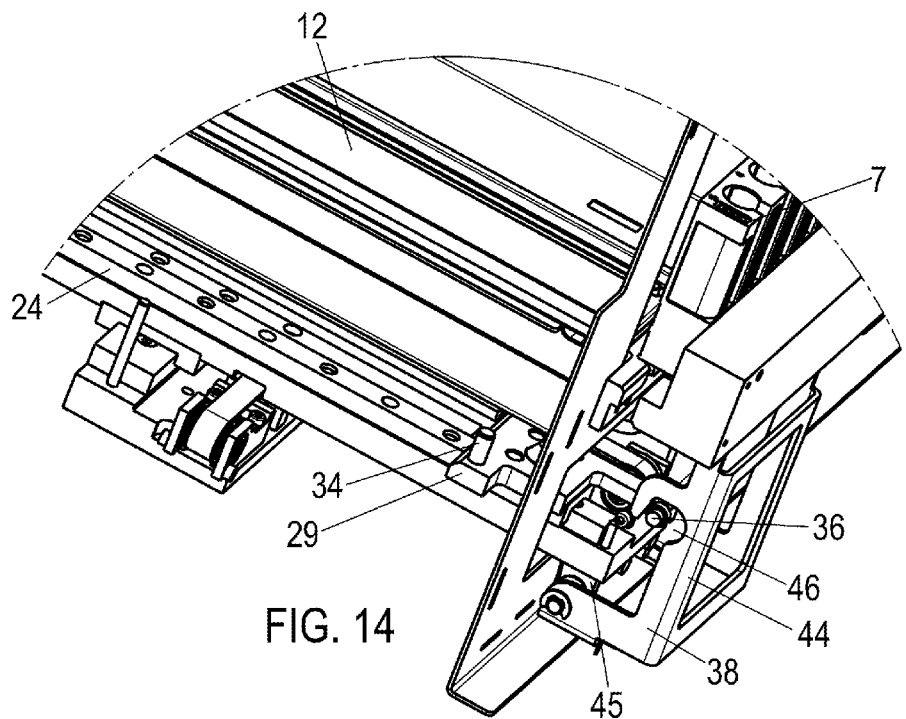
FIG. 14 illustrates an enlarged detail of FIG. 13 according to an embodiment of the present disclosure.
Figure 15:
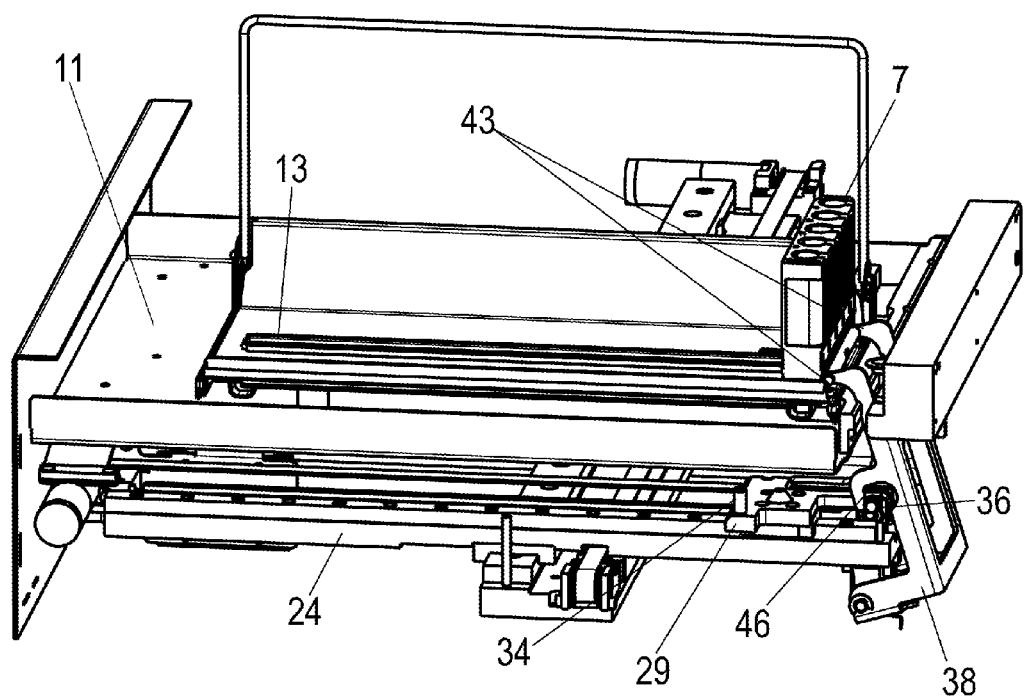
FIG. 15 illustrates another perspective view of the output carrier section of the sample unit of the instrument of FIG. 1 according to an embodiment of the present disclosure.

With reference to FIGS. 13 to 15, each output carrier support 11 can comprise an output pusher 38 for pushing tube racks 7 from the transfer lane 41 to a rack carrier 12 positioned on the output carrier support 11. The output pusher 38 can be provided with an output pusher contact face 43 positioned towards a tube rack 7 on the transfer lane 41 in front of the output pusher 38, with the output pusher 38 tiltable in the second horizontal direction (y) towards and away from the output carrier support 11. As a result, by tilting the output pusher 38 towards the output carrier support 11, the output pusher contact face 43 can be brought in contact with a tube rack 7 positioned on the transfer lane 41 in front of the output pusher 38 so as to push the tube rack 7 onto a rack carrier 12. In one embodiment, each output pusher 38 can comprise a pusher mount 44 provided with an output pusher contact face 43, with the pusher mount 44 tiltably fixed to a base 45 of the output carrier section 9.

The output pusher 38 can be pivoted by the first tube rack transfer device 2. The output pusher control pin 36 can be engaged with an output pusher control pin recess 46, which, in one embodiment, can be formed by a hook, by moving the transfer head 29 in the first horizontal direction (x). Having the output pusher control pin 36 inserted into the output pusher control pin recess 46, the output pusher 38 can be tilted towards the output carrier support 11 by moving the transfer head 29 in the second horizontal direction (y). The output pusher control pin 36 can also be used to move the output pusher 38 away from the output carrier support 11. Alternatively, in one embodiment, movement of the output pusher 38 towards the output carrier support 11 can be against the resilient force of a resilient element, so that the resilient force can be used to move the output pusher 38 back if the output pusher control pin 36 is out of contact with the output pusher control pin recess 46.

Figure 16:
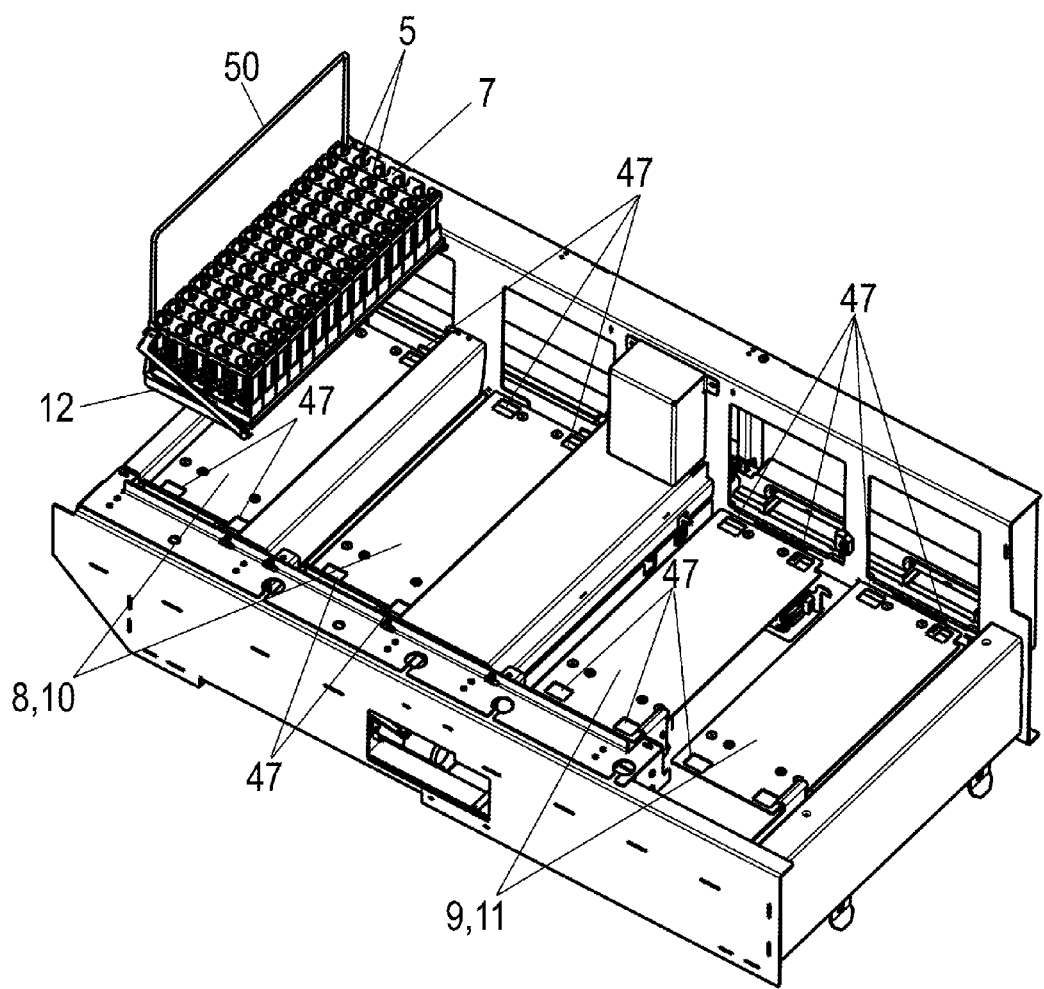
FIG. 16 illustrates a perspective view of the sample unit of the instrument of FIG. 1 illustrating the carrier sections according to an embodiment of the present disclosure.

With reference to FIG. 16, each carrier support 10, 11 can comprise one or more positioning elements 47 for the correct positioning of a rack carrier 12. In one embodiment, each carrier support 10, 11 can comprise a number of depressions for inserting corresponding projections of the rack carrier 12. In one embodiment, the rack carrier 12 can have a holding bow 50 for the manual transport thereof. In one embodiment, each carrier support 10, 11 can be provided with a sensor for detecting the presence of a rack carrier 12, for example, by detecting the holding bow 50.

Accordingly, tube racks 7 can be supplied to the instrument 1 by positioning a rack carrier 12 filled with tube racks 7 on an input carrier support 10. The tube racks 7 supplied can be transported to the sampling area 4 via the transfer lane 41 and the rack transport shuttle 42. Furthermore, tube racks 7 can be transported from the sampling area 4 to a rack carrier 12 on an output carrier support 11 so as to remove the rack carrier 12 together with tube racks 7.

Figure 17:
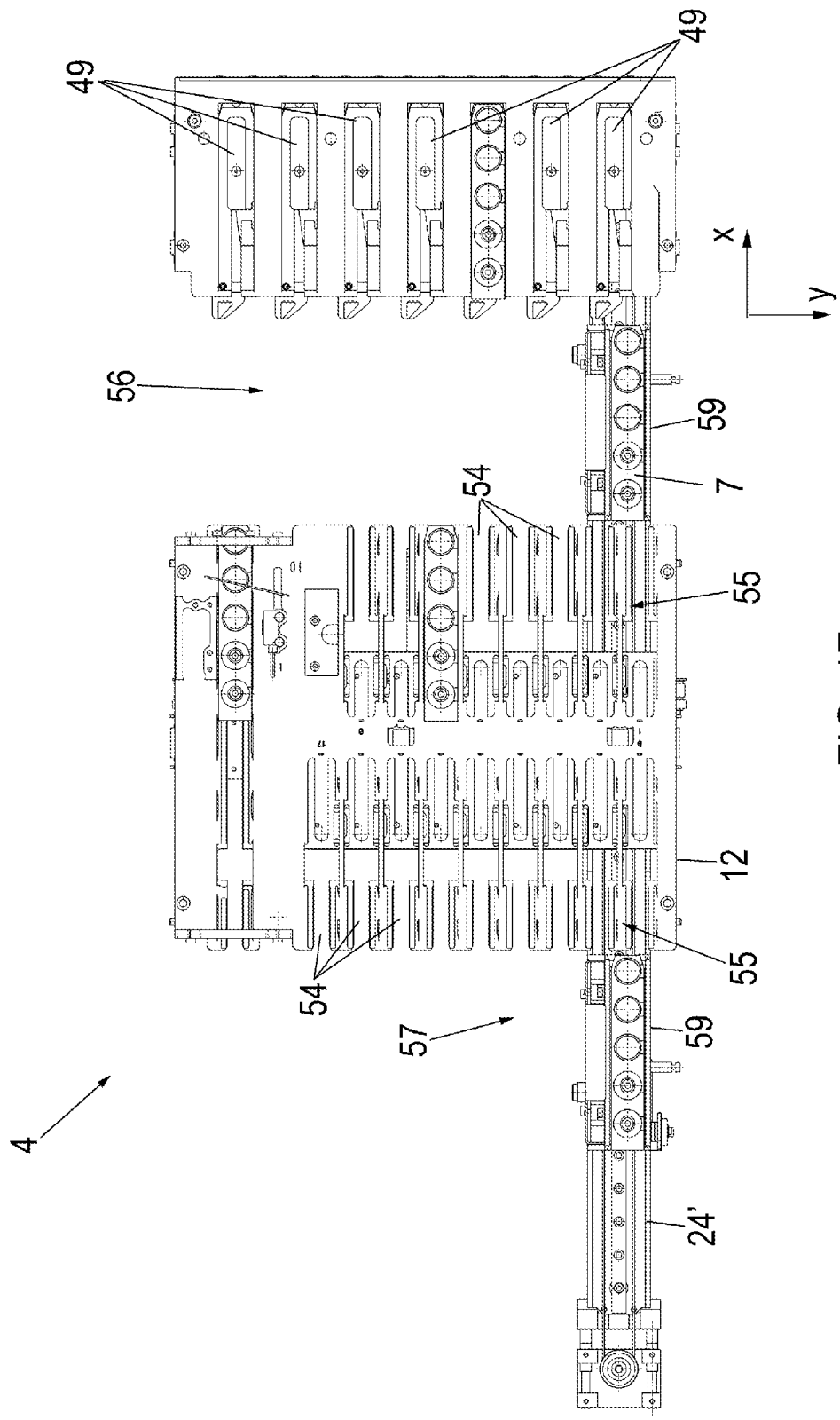
FIG. 17 illustrates a top view of the sampling area of the instrument of FIG. 1 according to an embodiment of the present disclosure.
Figure 18:
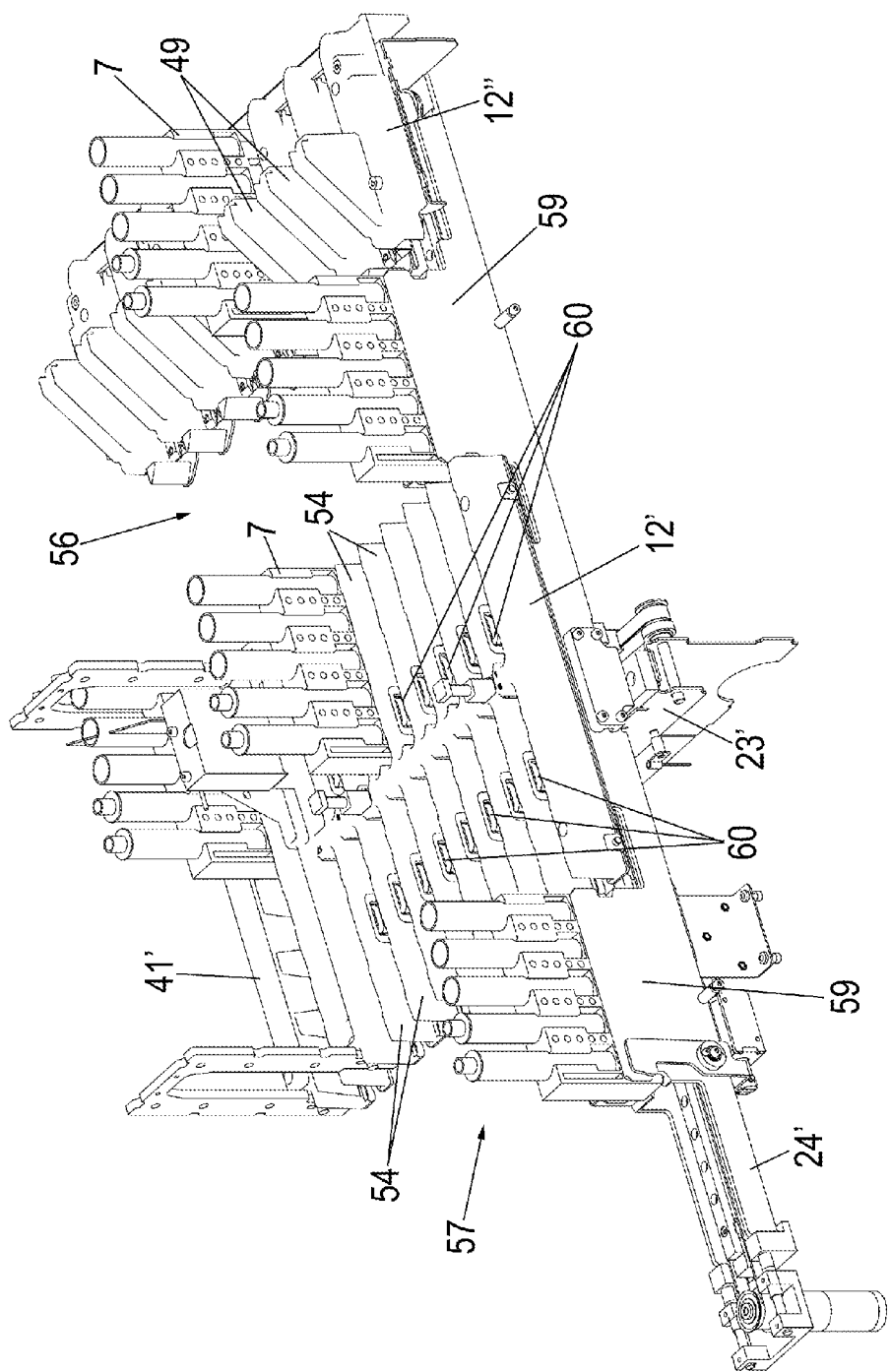
FIG. 18 illustrates a perspective view of the sampling area of FIG. 17 according to an embodiment of the present disclosure.
Figure 19:
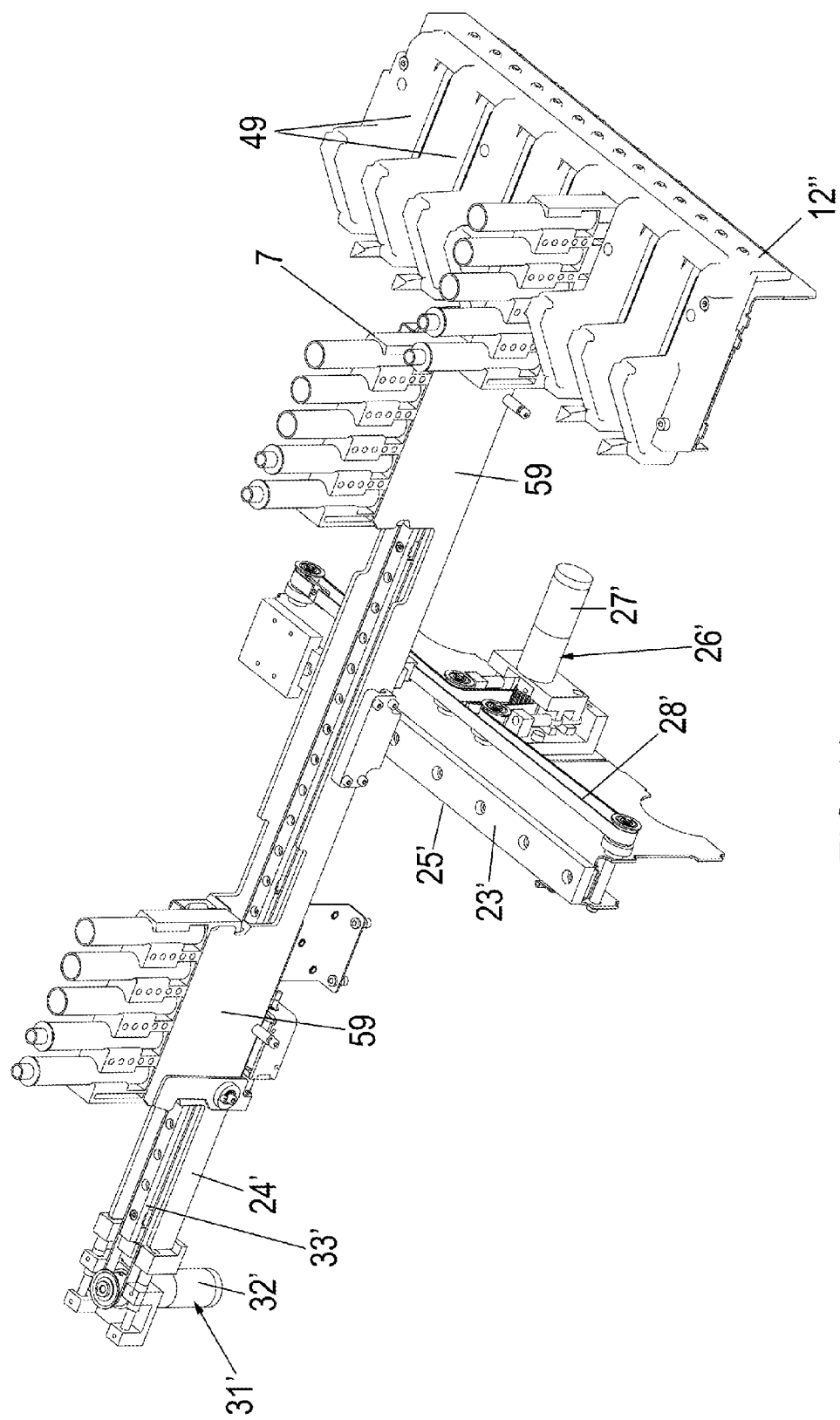
FIG. 19 illustrates another perspective view of the sampling area of FIG. 17 according to an embodiment of the present disclosure.
Figure 20:
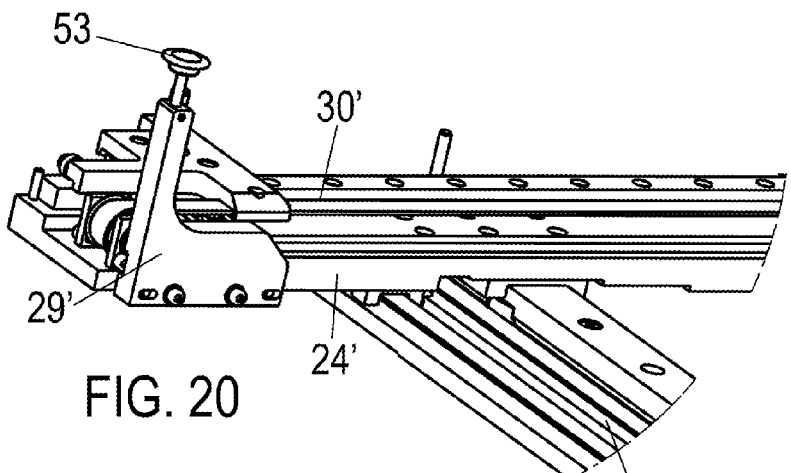
FIG. 20 illustrates a perspective view of the tube rack transfer device of the sampling area of the instrument of FIG. 1 according to an embodiment of the present disclosure.

With reference to FIGS. 17 to 19, the sampling area 4 can comprise a (non-removable) rack carrier 12' provided with a plurality of carrier slots 54 arranged in two slot rows 55, each of which extending in the second horizontal direction (y) and arranged side by side along the first horizontal direction (x). In addition, the sampling area 4 can comprise another rack carrier 12" with a plurality of input slots 49 arranged in a row extending along the second horizontal direction (y), with each of which can support a tube rack 7 for (manually) inputting tube racks 7 to the sampling area 4. Accordingly, tube racks 7 can be directly supplied to the sampling area 4 for preferentially analyzing samples, e.g. in urgent cases. A first free space 56 can be arranged in-between the rack carrier 12' and the input slots 49. Similarly, a second free space 57 can be arranged on the other side of the rack carrier 12'.

In the sampling area 4, tube racks 7 can be transported by the second tube rack transfer device 2' comprising a horizontal two-rail moving mechanism. With reference to FIGS. 19 to 22, the second tube rack transfer device 2' can comprise a first rail 23' extending in the second horizontal direction (y) and a second rail 24' extending in the first horizontal direction (x), with the second rail 24' translatably fixed to the first rail 23' so as to be translatable along the first rail 23'. The first rail 23' can be provided with a rail guide 25' extending along the first rail 23' for guiding the second rail 24', with the second rail 24' engaged with the rail guide 25'. Accordingly, the second rail 24' can be translated along the first rail 23'. With reference to FIG. 19, a first moving mechanism 26', e.g., a first electric motor 27' rotatably coupled to a first belt drive 28', can be operated to automatically translate the second rail 24' along the first rail 23'.

The second rail 24' can be provided with a transfer head 29', with the transfer head 29' translatably fixed to the second rail 24' so as to be translatable along the second rail 24'. The second rail 24' can be provided with a transfer head guide 30' extending along the second rail 24' for guiding of the transfer head 29', with the transfer head 29' engaged with the transfer head guide 30'. Accordingly, the transfer head 29' can be translated along the second rail 24'. With reference to FIG. 19, a second moving mechanism 26', e.g., a second electric motor 28' rotatably coupled to a second belt drive 33', can be operated to translate the transfer head 29' along the second rail 24'. Accordingly, the transfer head 29' can be moved over a horizontal plane having components of travel in the first horizontal direction (x) and/or the second horizontal direction (y).

Figure 21:
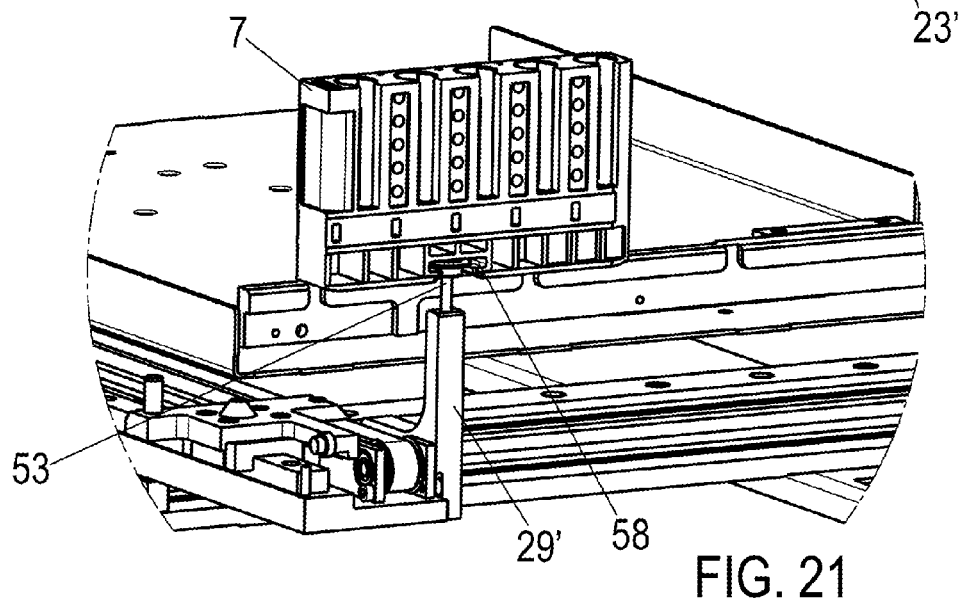
FIG. 21 illustrates a perspective view of the tube rack transfer device of FIG. 20 coupled to a rack carrier according to an embodiment of the present disclosure.
Figure 22:
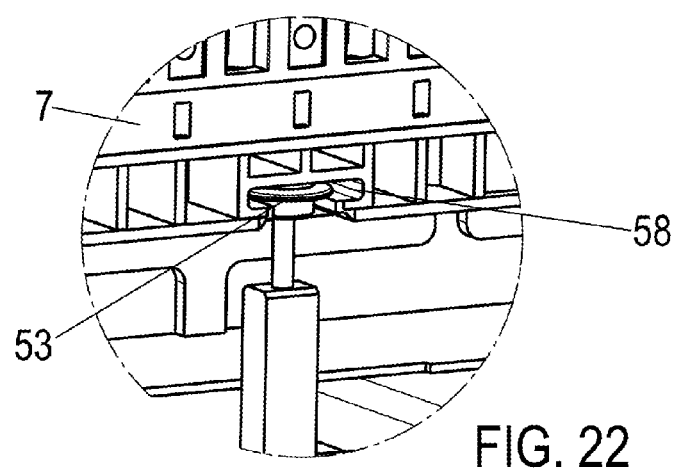
FIG. 22 illustrates an enlarged detail of FIG. 21 according to an embodiment of the present disclosure.

In one embodiment, the transfer head 29' can be provided with a rack control pin 53 for controlling movements of the tube racks 7. In the embodiment shown, the rack control pin 53 can project orthogonally relative to the horizontal plane spanned by the first and second horizontal directions (x, y). As illustrated in FIGS. 21 and 22, the rack control pin 53 can brought in engagement with a tube rack recess 58 of a tube rack 7 for moving the tube rack 7. The rack control pin 53 can be used analogously to the transfer lane pin 37 by directly interacting with a tube rack 7.

With continued reference to FIGS. 18 and 19, the second rail 24' can be moved along the second horizontal direction (y) along the extension of the slot rows 55 of the carrier slots 54. The second rail 24' can be provided with two rail slots 59, each of which can support a tube rack 7 and can be arranged in the first and second free spaces 56, 57, respectively. Accordingly, the rail slots 59 can be aligned with both a carrier slot 54 and an input slot 49 by moving the second rail 24' along the second horizontal direction (y). As a result, a tube rack 7 can readily be transported from an input slot 49 to a carrier slot 54 via the rail slot 59 arranged therebetween by moving the rack control pin 53 along the second rail 24'. Moreover, a tube rack 7 can be transported from one carrier slot 54 to another carrier slot 54 via one rail slot 59. As can best be seen in FIG. 18, the rack control pin 53 can be moved from one carrier slot 54 to another carrier slot 54 via pin holes 60. Accordingly, the rack control pin 53 can be disengaged from a tube rack 7 in a carrier slot 54 for leaving the tube rack 7 in the carrier slot 54. Furthermore, the rack control pin 53 can be engaged with a tube rack 7 in a carrier slot 54 for moving the tube rack 7 out of the carrier slot 54.

Similarly, the rack control pin 53 can be engaged with a rack 7 in the rack transport shuttle 42 to transport tube racks 7 from the sample unit 6 to the sampling area 4 and vice versa. A tube rack 7 can be transported from the rack transport shuttle 42 to a carrier slot 54, or vice versa, by transferring the tube rack 7 via a rail slot 59. In the sampling area 4, a tube rack 7 can also be transported from a carrier slot 54 in one slot row 55 to another carrier slot 54 in another slot row 55, or from an input slot 49 to a carrier slot 54 via a transfer lane 41'.

Accordingly, tube racks 7 can readily be transported between the sampling unit 6 and the sampling area 4 and within the sampling area 4 by using the two tube rack transfer devices 2, 2' which can have a similar construction.

With continued reference to FIG. 1, a controller 48 can be setup for the automated transfer of tube racks 7 in the diagnostic instrument 1. Specifically, if a rack carrier 12 with tube racks 7 is put on an input carrier support 10 (with the input pusher 15 in the parking area 51), the input pusher 15 can be moved towards the transfer lane 41 until it gets into contact with the closest tube rack 7 on the rack carrier 12. The position of the input pusher 15 reached can be used to automatically identify the presence and number of tube racks 7 on the rack carrier 12 supplied. Then, the input pusher control pin 34 can be engaged with the input pusher 15 and, simultaneously, the input pusher fixation mechanism 52 can be released by the input pusher fixation control pin 35, followed by moving the transfer head 29 towards the transfer lane 41 so as to push the first tube rack 7 (farthest away from the input pusher 15) on the transfer lane 41. The tube rack 7 pushed on the transfer lane 41 can be automatically engaged with the transfer lane pin 37 due to the position of the transfer lane pin 37 without moving the second rail 24. Now, by moving the second rail 24 along the first horizontal direction (x), the tube rack 7 can be transported to the rack transport shuttle 42 so as to continue transport with rack transport shuttle 42. The rack transport shuttle 42 can be moved to the sampling area 4 for transferring a tube rack 7 to the tube rack transfer device 2' for being transferred to a slot 54. Then, a tube rack 7 can be transported from the sampling area 4 to the transfer lane 41 via the rack transport shuttle 42 by operating the second tube rack transfer device 2' so as to be brought in contact with the transfer lane pin 37. Now, by moving the second rail 24 along the first horizontal direction (x), the tube rack 7 can be transported in a position in front of an output pusher 38. Then, the output pusher control pin 36 can be engaged with the output pusher 38 so as to tilt the output pusher 38 towards a rack carrier 12 on an output carrier support 11 to push the tube rack 7 on the rack carrier 12. Furthermore, the controller 48 can be setup to select a carrier slot 54 based on the availability of the carrier slot 54 and/or a travel distance to reach the carrier slot 54.

Similarly, further tube racks 7 on the rack carrier 12 in the input carrier section 8 can be transported to the sampling area 4 until no tube rack 7 is present on the rack carrier 12. In one embodiment, a rack carrier 12 in the output carrier section 9 can be completely filled to then be removed manually from the output carrier section 9. A sensor arranged in correspondence with an output carrier section 9 can be used to identify a filling degree of a rack carrier 12. Furthermore, the number of tube racks 7 pushed on the rack carrier 12 can be counted.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Obviously, many modifications and variations of the present invention are possible in light of the above description. It is therefore to be understood, that within the scope of appended claims, the present disclosure may be practiced otherwise than as specifically devised. For instance, instead of having a dedicated input carrier section 8 and output carrier section 9, one carrier section can be used for the input and/or output of rack carriers 12. Moreover, a same rack carrier 12 can be used for both supplying and receiving of tube racks 7.

As described, the instrument 1 can have many advantages over the prior art. A major advantage can be given by the fact that the instrument can be simple and robust in construction by having tube rack transfer devices provided with only a few number of components. The transport of tube racks with respect to plural carrier sections and rack carriers, respectively, can be performed by only one movable transfer head provided with control pins which can be controlled by only two electric motors. Accordingly, the transport of tube racks can easily be controlled. Furthermore, due to a comparably low number of components, the instrument can be produced at low-cost and can be suitable for long-term maintenance-free usage. As a result, samples can be processed in a highly cost-efficient manner.

The invention claimed is:

1. An in-vitro diagnostic instrument, the in-vitro diagnostic instrument comprising:
   at least one rack carrier comprising a tube rack guide for guiding tube racks in a row, wherein the rack carrier is configured to receive the tube racks along an extension of the rack carrier with tube seats of the tube rack arranged perpendicular to the extension of the rack carrier;
   at least one analyzer of the in-vitro diagnostic instrument for carrying out in-vitro diagnostic tests on biological samples;
   a sampling area of the in-vitro diagnostic instrument comprising at least one tube rack receiving position accessible for withdrawing samples from sample tubes, the sampling area being positioned between the at least one analyzer and at least one sample unit for inputting/outputting tube racks, wherein the sample unit comprises
      an input carrier section provided with one or more input carrier supports, each of which is adapted for supporting at least one rack carrier for holding tube racks to be supplied to the sampling area; and
      an output carrier section provided with one or more output carrier supports, each of which is adapted for supporting a rack carrier for holding tube racks to be received from the sampling area or the input carrier section;
   a transfer lane coupled to the input carrier section and to the output carrier section to transfer tube racks from the input carrier section to the sampling unit or output carrier section and to transfer tube racks from the sampling unit to the output carrier section; and
   at least one tube rack transfer device for transferring tube racks in the input carrier section and the output carrier section, the tube rack transfer device comprising:
   a first rail extending in a first horizontal direction,
   a second rail extending in a second horizontal direction orthogonal to the first horizontal direction, wherein the second rail is movable along the first rail and comprises at least one transfer head movable along the second rail, wherein the transfer head comprises at least one control pin,
   an input pusher coupled to and engaged with the transfer head of the input carrier support by at least one control pin, the input pusher comprising an input pusher contact face positioned towards a rack carrier and the sampling area, wherein the input pusher is translatable in the second horizontal direction for transferring a tube rack with the input pusher contact face from the rack carrier positioned on the input carrier support towards and onto the transfer lane to be transferred into the sampling area of the diagnostic instrument,
   an output pusher coupled to and engaged with the transfer head of the output carrier support by at least one control pin, the output pusher comprising an output pusher contact face positioned towards a tube rack on the transfer lane in the sampling area of the diagnostic area for transferring the tube rack from the sampling area of a diagnostic instrument to a rack carrier positioned on the output carrier support with the output pusher contact face as the transfer head of the output carrier support moves away from the transfer lane, and
   a tube rack for transferring the tube rack between different rack carriers and/or between different positions of the rack carrier, and
   wherein the at least one control pin is adapted to be coupled with at least the input pusher, the output pusher, the tube rack, and combinations thereof.

2. The in-vitro diagnostic instrument according to claim 1, wherein the
   transfer lane extends along the first horizontal direction and arranged between at least two rack carriers or slot rows of a rack carrier from the input carrier section to the output carrier section adjacent the sampling area, wherein the slot rows accept tube racks and wherein the slot rows extend in the second horizontal direction and are arranged side by side along the first horizontal direction so that a tube rack can be transferred between different rack carriers and/or between a rack carrier and the sampling area via the transfer lane and/or within the sampling area via the transfer lane.

3. The in-vitro diagnostic instrument according to claim 2, wherein the second rail comprises a transfer lane pin linearly translatable together with the second rail in the first horizontal direction for moving a tube rack along the transfer lane.

4. The in-vitro diagnostic instrument according to claim 1, wherein the transfer head comprises an input pusher control pin adapted to be coupled with at least one input pusher and an output pusher control pin adapted to be coupled with at least one output pusher.

5. The in-vitro diagnostic instrument according to claim 1, wherein the transfer head comprises an input pusher fixation control pin adapted to be coupled with at least one input pusher by contacting a turning lever of the at least one input pusher for releasing a fixation crotchet of a fixation mechanism, wherein the fixation crotchet engages with a fixation recess on the second rail, preventing the input pusher to be translated in the second direction.

6. The instrument according to claim 1, wherein each rack carrier comprises a rack guide for guiding tube racks.

7. The instrument according to claim 6, wherein tube racks in the rack carrier are aligned in a row.

8. The instrument according to claim 1, further comprising a first tube rack transfer device arranged underneath the sample unit and a second tube rack transfer device arranged underneath the sampling area.

9. The instrument according to claim 2, further comprising,
a rack transport shuttle for transporting a tube rack received/provided from/to the transfer lane, wherein the transfer lane receives the tube rack from the input carrier section and provides the tube rack to the output carrier section.

10. The instrument according to claim 1, wherein the output pusher contact face of the output pusher is tiltable in the second direction for pushing tube racks.

11. The instrument according to claim 1, wherein the sampling area comprises an internal, non-removable rack carrier, wherein the sampling area rack carrier comprises one or more input slots for supporting tube racks.

12. The instrument according to claim 1, wherein the sampling area comprises an internal, non-removable rack carrier, wherein the sampling area rack carrier comprises a plurality of carrier slots for receiving tube racks into the sampling area rack carrier from the transfer lane, wherein the carrier slots are arranged in at least two slot rows, wherein the slot rows extend in the second horizontal direction and are arranged side by side along the first horizontal direction.

13. The instrument according to claim 12, wherein the carrier slots of the sampling area rack carrier are coupled to the transfer lane extending along the slot rows so as to transfer tube racks from a carrier slot of a first slot row to a carrier slot of second slot row.

* * * * *